(12) United States Patent
Orrico et al.

(10) Patent No.: US 7,766,016 B2
(45) Date of Patent: Aug. 3, 2010

(54) ANTI-SNORING DEVICE

(75) Inventors: Anthony J. Orrico, Jupiter, FL (US);
Neal Rosenblum, Hollywood, FL (US)

(73) Assignee: Anthony J. Orrico, LLC, Jupiter, FL (US)

( * ) Notice: Subject to any disclaimer, the term of this patent is extended or adjusted under 35 U.S.C. 154(b) by 74 days.

(21) Appl. No.: 12/157,797

(22) Filed: Jun. 13, 2008

(65) Prior Publication Data
US 2009/0308401 A1 Dec. 17, 2009

(51) Int. Cl.
A61F 5/56 (2006.01)
A61C 5/14 (2006.01)
A61C 3/00 (2006.01)

(52) U.S. Cl. .............................. 128/848; 128/859; 433/6

(58) Field of Classification Search ................ 128/848, 128/859–862, 846; 433/6, 7, 19, 18, 24, 433/14; 602/902
See application file for complete search history.

(56) References Cited

U.S. PATENT DOCUMENTS

| | | | |
|---|---|---|---|
| 5,082,007 A | 1/1992 | Adell | |
| 5,365,945 A | 11/1994 | Halstrom | |
| 5,499,633 A * | 3/1996 | Fenton | 128/848 |
| 5,566,683 A | 10/1996 | Thornton | |
| 5,611,355 A | 3/1997 | Hilsen | |
| 5,823,193 A | 10/1998 | Singer et al. | |
| 5,868,138 A | 2/1999 | Halstrom | |
| 5,884,628 A * | 3/1999 | Hilsen | 128/848 |
| 5,941,247 A | 8/1999 | Keane | |
| 6,055,986 A | 5/2000 | Meade | |
| 6,170,485 B1 * | 1/2001 | Orrico | 128/848 |
| 2003/0217753 A1 | 11/2003 | Thornton | |

* cited by examiner

*Primary Examiner*—Patricia M Bianco
*Assistant Examiner*—Ophelia Hawthorne
(74) *Attorney, Agent, or Firm*—George Pappas

(57) ABSTRACT

An anti-snoring device including first and second arcuate members. The first member defines a receptacle for receiving teeth located on either of the user's upper or lower jaw, and a first plurality of fasteners on an opposite side and extending outwardly therefrom. The second member defines a receptacle for receiving teeth located on the other of the user's upper or lower jaws, and a second plurality of fasteners on an opposite side and extending outwardly therefrom. The first and second plurality of fasteners are each formed by elongate, parallel extending projections that define voids therebetween. Selective engagement of the projections and voids allows the first and second members to be secured together in a plurality of different relative positions.

21 Claims, 3 Drawing Sheets

ANTI-SNORING DEVICE

BACKGROUND OF THE INVENTION

1. Field of the Invention

The present invention relates to dental devices used for the alleviation of snoring. More particularly, the present invention relates to a device for positioning a person's lower jaw in a relatively forward position to thereby alleviate snoring.

2. Description of the Related Art

Snoring is a problem suffered by a large number of people. In many cases, snoring is caused by the relaxation of the tongue and the resulting blockage of the breathing airway. When the tongue of the sleeping individual relaxes and creates such a blockage and the individual subsequently forcibly passes air through the breathing airway, loud vibrations between the tongue and surrounding tissues will often result in the noises commonly referred to as snoring.

It is known that such snoring can be alleviated by displacing the individual's lower jaw into a position that is relatively forward of its normal position. A variety of known devices are designed to forwardly displace an individual's lower jaw while they are sleeping to thereby alleviate snoring. While many such devices would appear to be effective for alleviating snoring, an improved device which can be cost-effectively manufactured and can be easily adjusted and used by the end-user is desirable.

SUMMARY OF THE INVENTION

The present invention provides a user-friendly anti-snoring device that can be cost-effectively manufactured.

The invention comprises, in one form thereof, an anti-snoring device for mounting on the teeth of a user's upper and lower jaws. The device includes first and second arcuate members. The first member has a first side and an opposite second side wherein the first side defines a receptacle for receiving at least a portion of the teeth of either the user's upper or lower jaw and the second side of the first member has a first plurality of fasteners projecting outwardly therefrom. The first plurality of fasteners are formed by a plurality of elongate, parallel extending first projections that define voids between adjacent ones of the first projections. The first projections extend in a direction substantially transverse to a centerline of the device. The second member has a first side and an opposite second side wherein the first side defines a receptacle for receiving at least a portion of the teeth of the other of the user's upper or lower jaws, and the second side has a second plurality of fasteners projecting outwardly therefrom. The second plurality of fasteners are formed by a plurality of elongate, parallel extending second projections that define voids between adjacent ones of the first projections. The second projections extend in a direction substantially transverse to a centerline of the device. The first and second plurality of fasteners are selectively mutually engageable by disposing at least one of the first projections into a void defined between the second projections and disposing at least one of the second projections into a void defined between the first projections whereby the first and second members can be secured together in a plurality of configurations defining a plurality of relative positions between the user's upper and lower jaws when the first and second members are mounted thereon.

The invention comprises, in another form thereof, an anti-snoring device for mounting on the teeth of a user's upper and lower jaws. The device includes first and second arcuate members. The first member has a first side and an opposite second side wherein the first side defines a receptacle for receiving at least a portion of the teeth of either the user's upper or lower jaw and the second side of the first member has a first plurality of fasteners projecting outwardly therefrom. The first plurality of fasteners are formed by a plurality of elongate, parallel extending first projections that define voids between adjacent ones of the first projections. Each of the first projections has a neck portion and a retaining head wherein the retaining head is disposed distal of the neck portion and has a width greater than the neck portion. The second member has a first side and an opposite second side wherein the first side defines a receptacle for receiving at least a portion of the teeth of the other of the user's upper or lower jaws, and the second side has a second plurality of fasteners projecting outwardly therefrom. The second plurality of fasteners are formed by a plurality of elongate, parallel extending second projections that define voids between adjacent ones of the first projections. Each of the second projections has a neck portion and a retaining head wherein the retaining head is disposed distal of the neck portion and has a width greater than the neck portion. The first and second plurality of fasteners are selectively mutually engageable by disposing at least one of the first projections into a void defined between the second projections and disposing at least one of the second projections into a void defined between the first projections whereby the first and second members can be secured together in a plurality of configurations defining a plurality of relative positions between the user's upper and lower jaws when the first and second members are mounted thereon.

The invention comprises, in yet another form thereof, an anti-snoring device for mounting on the teeth of a user's upper and lower jaws. The device includes first and second arcuate members wherein each of the first and second arcuate members has a substantially common design. The first member has a substantially C-shaped cross section defining a receptacle for receiving at least a portion of the teeth of either the user's upper or lower jaw. The first member also has a first plurality of fasteners disposed on the C-shaped cross section opposite an opening of the receptacle and projecting outwardly from the first member. The first plurality of fasteners are formed by a plurality of elongate, parallel extending first projections that define voids between adjacent ones of the first projections. The first projections extend in a direction substantially transverse to a centerline of the device and each of the first projections has a neck portion and a retaining head wherein the retaining head is disposed distal of the neck portion and has a width greater than the neck portion. The second arcuate member has a substantially C-shaped cross section defining a receptacle for receiving at least a portion of the teeth of the other of the user's upper or lower jaws. The second member further includes a second plurality of fasteners disposed on the C-shaped cross section opposite an opening of the receptacle and projecting outwardly from the second member. The second plurality of fasteners are formed by a plurality of elongate, parallel extending second projections that define voids between adjacent ones of the second projections. The second projections extend in a direction substantially transverse to a centerline of the device and each of the second projections has a neck portion and a retaining head wherein the retaining head is disposed distal of the neck portion and has a width greater than the neck portion. The first and second plurality of fasteners are selectively mutually engageable by disposing at least one of the first projections into a void defined between the second projections and disposing at least one of the second projections into a void defined between the first projections thereby placing at least a portion of the retaining heads of the first and second plurality of fasteners into mutual engagement and securing the first arcuate member relative to the second arcuate member. The first and second members being selectively securable together in a plurality of configurations defining a plurality of relative positions between the user's upper and lower jaws when the first and second members are mounted thereon.

BRIEF DESCRIPTION OF THE DRAWINGS

The above mentioned and other features of this invention, and the manner of attaining them, will become more apparent and the invention itself will be better understood by reference to the following description of embodiments of the invention taken in conjunction with the accompanying drawings, wherein.

Figure 1:
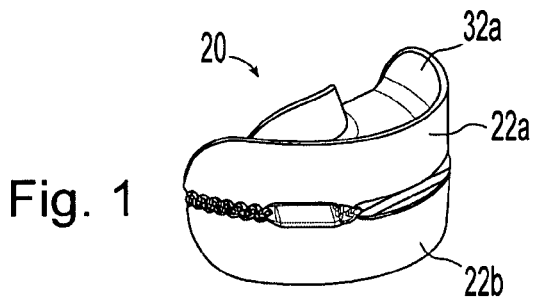
FIG. 1 is a perspective view of an anti-snoring device in a first configuration.
Figure 2:
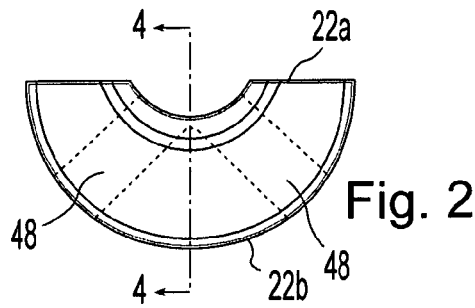
FIG. 2 is a top view of the device in the first configuration.
Figure 3:
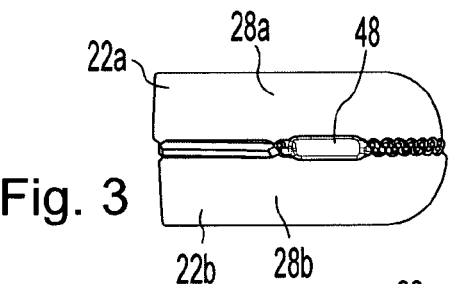
FIG. 3 is a side view of the device in the first configuration.

Corresponding reference characters indicate corresponding parts throughout the several views. Although the exemplification set out herein illustrates embodiments of the invention, in several forms, the embodiments disclosed below are not intended to be exhaustive or to be construed as limiting the scope of the invention to the precise forms disclosed.

DETAILED DESCRIPTION OF THE INVENTION

One embodiment of an anti-snoring device 20 in accordance with the present invention is depicted in FIG. 1. Device 20 includes an upper arcuately shaped member 22a and a lower arcuately shaped member 22b. The arcuate, or horseshoe-like, shape of members 22a, 22b adapt members 22a, 22b for respective mounting on the teeth of a user's upper and lower jaws. Arcuate members 22a, 22b are injection molded and made of a generally rigid plastic material.

In the embodiment illustrated in FIG. 1, members 22a, 22b each have a substantially common design and the use of the suffixes "a" and "b" is merely used to indicate that when in use, one of the members 22a, 22b will be mounted on the user's upper jaw while the other will be mounted on the user's lower jaw. As used herein, common reference numerals indicate common structures even though such reference numerals may employ different letter suffixes or no letter suffix at all.

While the embodiment illustrated in FIG. 1 utilizes two arcuate members 22a, 22b having a common design to form anti-snoring device 20, the present invention also encompasses anti-snoring devices which utilize two distinct designs for the two arcuate members. By utilizing two arcuate members which have a common design as exemplified in FIG. 1, a number of efficiencies can be obtained. For example, a single mold, rather than two separate molds, can be used to manufacture the arcuate members. The necessity to coordinate the manufacture of an equal number of the two different designs is eliminated when both arcuate members have a common design. Moreover, the packaging of individual sets of two arcuate members to form an anti-snoring device is simplified when the members have a common design.

Not shown in FIGS. 1-12 is a moldable material 58 which is located in receptacles 32a, 32b formed by arcuate members 22a, 22b. As discussed in greater detail below, moldable material 58 is used to fit members 22a, 22b to the intended user's upper and lower teeth respectively. This differential customization of members 22a, 22b, however, is a post-manufacturing and distribution activity carried out by the end user and such fitted members 22a, 22b have a "common design" as this phrase is used herein. This fitting of the members 22a, 22b to the upper and lower teeth of the user may also be done under the guidance of a professional, however, such customization is so easy to perform that the assistance of a professional is unnecessary.

Figure 4:
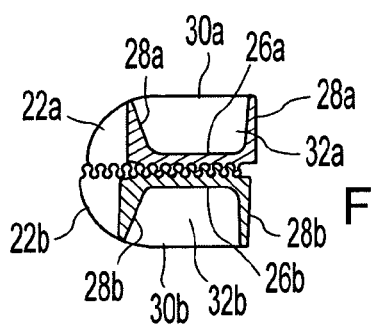
FIG. 4 is a cross sectional view taken along line 4-4 of FIG. 2.
Figure 5:
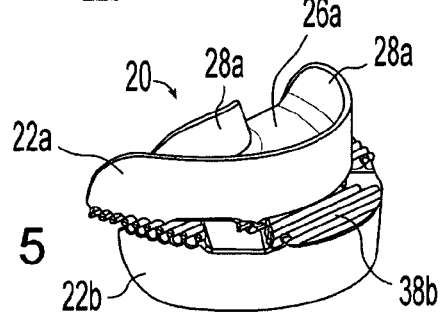
FIG. 5 is a perspective view of the device in a second configuration.
Figure 6:
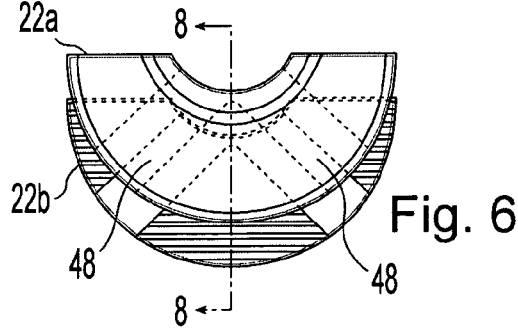
FIG. 6 is a top view of the device in the second configuration.
Figure 7:
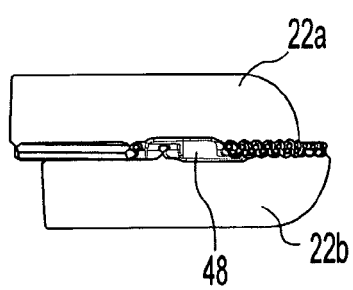
FIG. 7 is a side view of the device in the second configuration.
Figure 8:
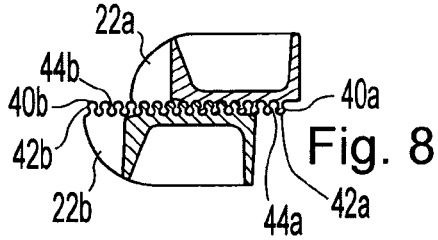
FIG. 8 is a cross sectional view taken along line 8-8 of FIG. 6.
Figure 9:
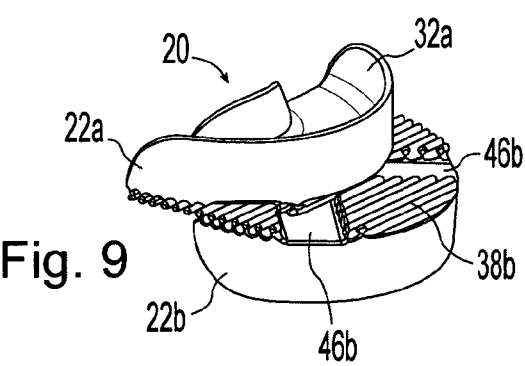
FIG. 9 is a perspective view of the device in a third configuration.
Figure 10:
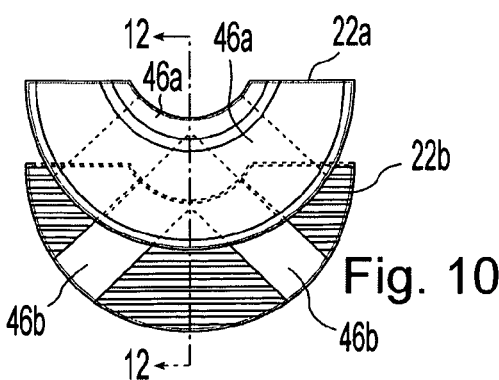
FIG. 10 is a top view of the device in the third configuration.
Figure 11:
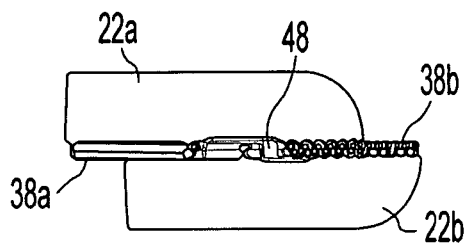
FIG. 11 is a side view of the device in the third configuration.
Figure 12:
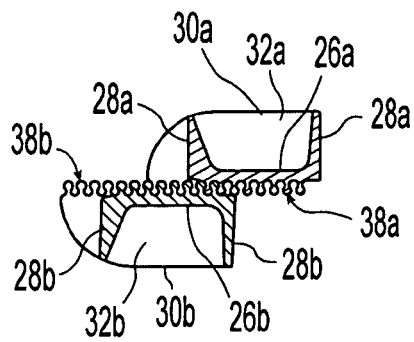
FIG. 12 is a cross sectional view taken along line 12-12 of FIG. 10.
Figure 13:
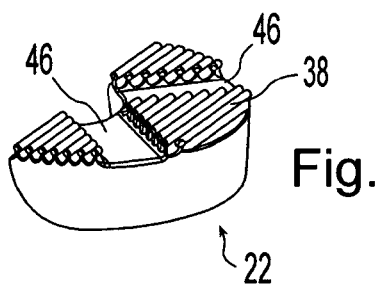
FIG. 13 is a perspective view of a single arcuate member of the device.
Figure 14:
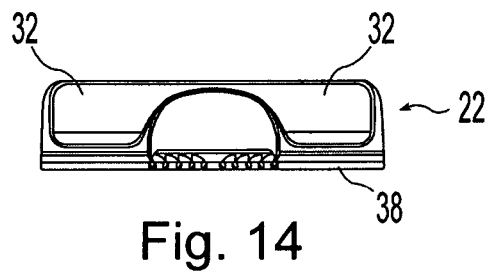
FIG. 14 is an end view of the arcuate member.

As can be seen in FIG. 4, members 22a, 22b each have a substantially C-shaped cross section defined by a central portion 26a, 26b and a pair of projecting limbs 28a, 28b. An opening 30a, 30b is defined between the distal ends of each of the respective pairs of limbs 28a, 28b and form receptacles 32a, 32b for receiving the users teeth as will be discussed in greater detail below. Openings 30a, 30b of receptacles 32a, 32b are formed on a first side 34a, 34b of members 22a, 22b while the opposite second side 36a, 36b of members 22a, 22b is defined a plurality of fasteners 38a, 38b.

Figure 20:
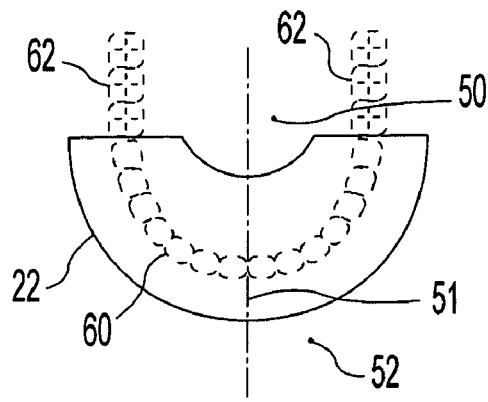
FIG. 20 is a schematic top view showing an arcuate member mounted on a user's lower jaw.

The plurality of fasteners 38a, 38b are formed by a series of elongate, parallel extending projections 40a, 40b. Projections 40a, 40b extend in a parallel direction generally transverse to centerline 51 (FIG. 20). Projections 40a, 40b have enlarged head portions 42a, 42b and define cooperating void spaces 44a, 44b between adjacent projections 40a, 40b. Projections 40a, 40b are received in the corresponding void spaces 44b, 44a of the other arcuate member to thereby secure the two arcuate members 22a, 22b together in a selected configuration. Because there is a limited number of parallel projections 40a, 40b and corresponding voids 44a, 44b, the two pluralities of fasteners 38a, 38b are securable together in a limited number of discrete configurations.

Figure 23:
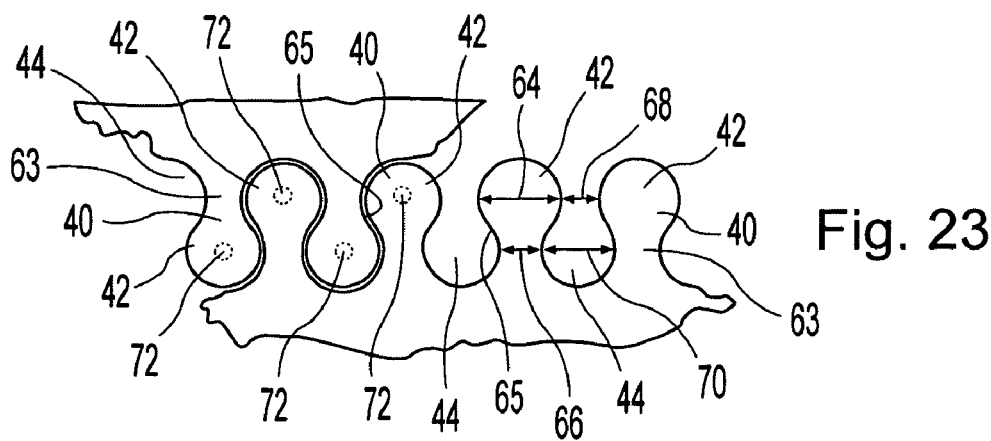
FIG. 23 is a detail view of the fasteners used to secure the arcuate members together.

Projections 40 are shown in a detail view in FIG. 23. (FIG. 23 corresponds to a cross sectional view taken along centerline 51.) Projections 40 each include a distal retaining head 42 defining a width 64 and a neck portion 63 defining a width 66. The retaining head 42 of each projection 40 is located distal relative to the neck portion 63 and defines a greater width 64 than the width 66 of neck portion 63. Voids 44 defined between adjacent projections 40 have a shape that allows projections 40 from the other arcuate member to be received therein with an enlarged portion defining a width 70 which is adapted to receive head portion 42 and a narrower opening defining a width 68 adapted to receive neck portion 63. In the illustrated embodiment, voids 44 have a shape that closely mirrors projections 40. In alternative embodiments, the voids may differ in shape from the projections provided that the insertion of the projections of one arcuate member into the voids of the other arcuate member secures the two members together. In this regard, it is noted that the engagement of laterally extending surfaces 65 on the underside of head portions 42 of the two arcuate members 22a, 22b secures the two arcuate members 22a, 22b together and inhibits their disassociation.

When securing the two arcuate members 22a, 22b together, at least one of the elongate projections 40 on each of the arcuate members 22a, 22b is inserted into at least one of the elongate, parallel extending voids 44 defined by adjacent projections 40 on the other of the arcuate members 22a, 22b. Projections 40 may be inserted into voids 44 by pressing projections 40 downwardly into voids 44 such that retaining heads 42 pass through the narrow opening having width 68. Since width 68 is smaller than the width of retaining head 42 in unstressed conditions, retaining heads 42 must be compressed in a width-wise direction, resulting in both a decrease in width 64 of retaining heads 42 and an increase in opening width 68, to allow for such insertion. Depending upon the compressibility of the material used to form retaining heads 42. Although the illustrated embodiment utilizes solid retaining heads 42, in some alternative embodiments, it may be desirable to place passages 72 through some or all of the retaining heads 42 on one or both of the members 22a, 22b for the full length of retaining heads 42 to thereby increase the compressibility of retaining heads 42 and facilitate the insertion and removal of heads 42 from voids 44. Dashed outlines are used to indicate optional passages 72 on several of the retaining heads in FIG. 23. It is also possible for arcuate members 22a, 22b to be secured together by aligning ends of projections 40 with voids 44 of the two members 22a, 22b and sliding projections 40 into position within voids 44 to thereby avoid the passage of retaining heads 42 through width 68. Such sliding engagement, however, would be more cumbersome to accomplish.

Typically, the lower jaw only needs to be shifted about 3-6 millimeters forward relative to its normal position and the range of discrete configurations in which members 22a, 22b can be secured advantageously provides for adjustment of members 22a, 22b over a range that extends over at least about 6 mm. FIGS. 1-12 illustrate device 20 in three separate configurations. FIGS. 1-4 illustrate members 22a, 22b secured together with only a minimal forward displacement of the lower member 22b. FIGS. 5-8 illustrate members 22a, 22b secured together with a moderate forward displacement of the lower member 22b. FIGS. 9-12 illustrate members 22a, 22b secured together with a large forward displacement of the lower member 22b. Individuals who snore typically prefer breathing through their mouth when sleeping and device 20 provides airway passages to facilitate the user's ability to breath through their mouth while using device 20.

The illustrated arcuate members 22a, 22b each include substantially unobstructed passageways 46a, 46b that define an airway passage between members 22a, 22b when device 20 is in use. As most easily seen in FIGS. 3, 7 and 9, when members 22a, 22b are secured together, passageways 46a, 46b are in communication and together form a common passageway 45. When in use, common passageway 48 provides a breathing airway across the width of device 20, i.e., from a central interior position 50 (FIG. 20) relative to members 22a, 22b to an exterior position 52 (FIG. 20) relative to members 22a, 22b, to thereby facilitate the user's ability to breath through their mouth. Although the illustrated embodiment employs members 22a, 22b having a common design with each of the members 22a, 22b defining passageways 46a, 46b, alternative embodiments which utilize arcuate members having different designs may employ arcuate members wherein only one of the arcuate members defines a substantially unobstructed passageway for facilitating the user's ability to breath through their mouth. In still other embodiments of the present invention, neither of the arcuate members may have a substantially unobstructed passageway for forming a breathing airway. In such embodiments where neither arcuate member includes an unobstructed passageway, the two members forming the anti-snoring device may have a substantially common design, or, may utilize two distinct designs.

Figure 15:
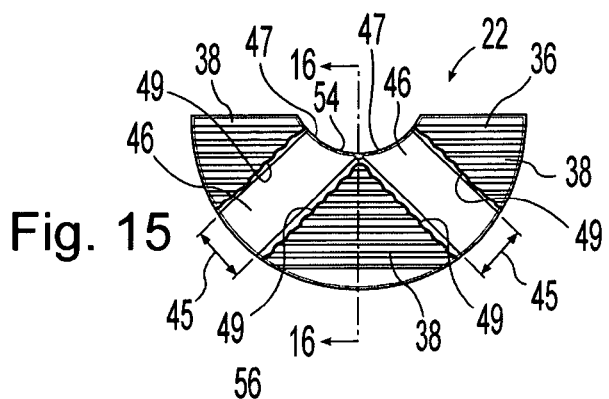
FIG. 15 is a bottom view of the arcuate member.
Figure 16:
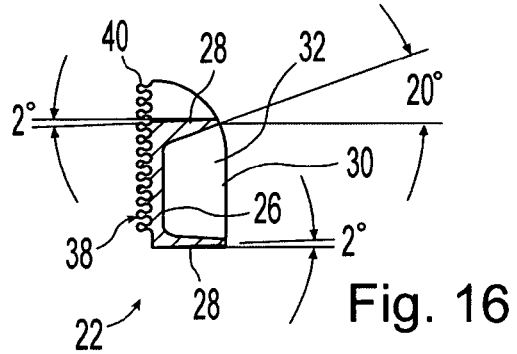
FIG. 16 is a cross sectional view taken along line 16-16 of FIG. 15.
Figure 17:
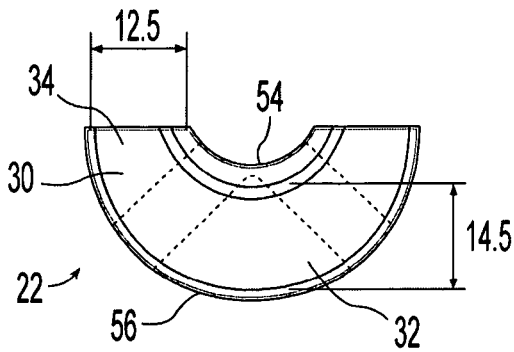
FIG. 17 is a top view of the arcuate member.
Figure 18:
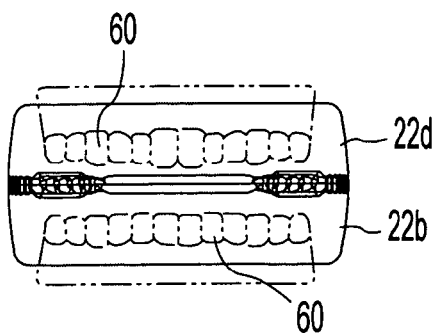
FIG. 18 is a schematic view showing the device in use.

In the embodiment depicted in FIGS. 1-18, each member 22a, 22b defines two substantially unobstructed passageways 46a, 46b which are arranged in a substantially V-shaped orientation. The V-shaped orientation of passageways 46 is most easily seen in FIG. 15. (A single arcuate member 22 which may be used to form either an upper or lower member is shown in FIGS. 13-17 and, thus, the reference numerals do not include suffixes.) As can also be seen in FIG. 15, side 36 of central portion 26 which is disposed opposite opening 30 of receptacles 32 defines a surface area 37 which is substantially entirely defined by the plurality of fasteners 38 and passageways 46. As also shown in FIG. 15, passageways 46 extend from an interior arcuate perimeter 54 of member 22 to an exterior arcuate perimeter 56 with the plurality of fasteners 38 positioned adjacent both edges 49 of passageways 46 for the full length of passageways 46. While the plurality of fasteners 38 extend along a majority of exterior perimeter 56, interior arcuate perimeter 54 has a smaller variable radius and openings 47 which passageways 46 form on interior arcuate perimeter 54 extend for a majority of interior arcuate perimeter 54. In embodiment illustrated in FIG. 15, passageways 46 have a width 45 which is sufficiently large that openings 47 extend not only for a majority of interior perimeter 54 but for substantially the entire interior perimeter 54. Passageways 46 may utilize various widths 45 including widths smaller than those employed with the illustrated embodiments. Advantageously, such passageway widths 45 are at least about 1 millimeter or greater.

Figure 19:
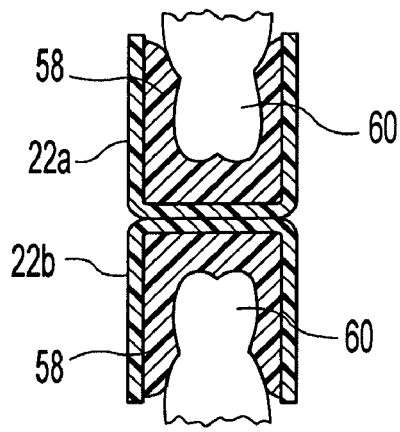
FIG. 19 is a schematic cross sectional view showing the device in use.

As shown in FIG. 19, a moldable material 58 can be disposed in receptacles 32 such that the receptacles are moldably conformable to the user's teeth 60. Moldable material 58 is not shown in the other figures for purposes of graphical clarity. Moldable material 58 is a thermoplastic material capable of being molded when heated to a temperature of greater than about 115° F. To fit members 22a, 22b to the end user's teeth 60, the end user, after purchasing a device 20, will place members 22a, 22b in water that has been heated to a temperature greater than 115° F. After members 22a, 22b, and the moldable material 58 in receptacles 32a, 32b, has been heated to a temperature greater than 115° F., the end user will remove members 22a, 22b from the heated water and place members 22a, 22b over the end user's teeth thereby causing moldable material 58 within receptacles 32a, 32b to be shaped or fitted to the user's teeth 60 on which the respective members will be mounted when device 20 is in use. Moldable material 58 may also be a chemical-set material, which would not require heating and cooling but, rather, time to set. The use of such moldable material 58 to fit a dental appliance to an end user's teeth is well known in the art.

As can be seen in FIG. 20, members 22 are mounted on the anterior teeth of the end user but do not extend to cover all of the user's posterior teeth 62. Alternative embodiments of the present invention, however, could employ larger arcuate members 22 that did extend to engage and cover all of the user's teeth.

Figure 21:
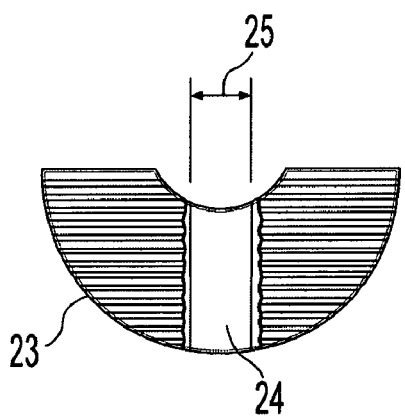
FIG. 21 is a bottom view of another arcuate member.
Figure 22:
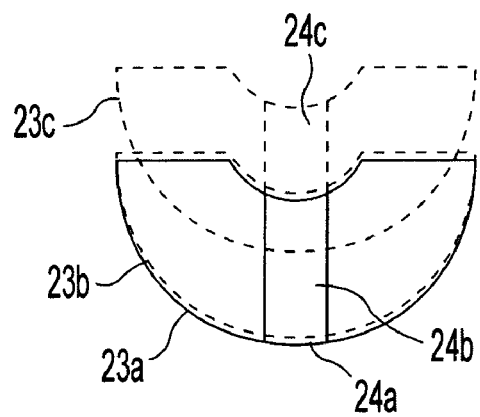
FIG. 22 is a schematic view illustrating different device configurations utilizing the arcuate member of FIG. 21.

A second embodiment of an arcuate member in accordance with the present invention is illustrated in FIGS. 21 and 22. This second embodiment utilizes arcuate members 23 having a common design and which are similar to arcuate members 22 except for the arrangement of substantially unobstructed passageway 24 on members 23. Instead of having two passageways arranged in a V-shaped pattern, arcuate members 23 have a single unobstructed passageway 24 that extends along the centerline of member 23 and has a width 25. Width 25 is sufficiently large that the opening of passageway 24 on the interior arcuate perimeter of member 23 extends over a majority of the interior arcuate perimeter of member 23. Unlike member 22, however, the opening of passageway 24 does not extend over the substantial entirety of the interior arcuate perimeter.

Members 23 may be secured together in a plurality of discrete positions in the same manner as arcuate members 22 and FIG. 22 schematically depicts a lower member 23a and the position of its passageway 24a and two alternative positions 23b and 23c of the upper member in dashed outlines and the positions of their respective passageways 24b, 24c. Dashed outline 23b depicts a configuration wherein the lower member 23a is displaced forwardly by only a minimal distance. Dashed outline 23c depicts a configuration wherein lower member 23a has been displaced forwardly by a large distance. As depicted in FIG. 22, by providing a passageway 24 that extends parallel with the direction of displacement, the width of the common passageway formed by the individual passageways 24 of the upper and lower members 23 remains at width 25 of the individual passageways 24 for the full range of displacement. In the embodiment of FIGS. 1-18 wherein members 22 have passageways 46 forming a V-shaped pattern, the overlap between the upper and lower passageways 46a, 46b becomes progressively smaller as the forward displacement of the lower member 22b is increased. This diminution of the common passageway does not occur for the embodiment of FIGS. 21 and 22 and, thus, the embodiment of FIGS. 21 and 22 can be beneficial for those individuals who need to utilize a large forward displacement of the lower jaw.

While this invention has been described as having an exemplary design, the present invention may be further modified within the spirit and scope of this disclosure. This application is therefore intended to cover any variations, uses, or adaptations of the invention using its general principles.

What is claimed is:

1. An anti-snoring device for mounting on the teeth of a user's upper and lower jaws, said device defining a centerline and comprising:

a first arcuate member having a first side and an opposite second side, said first side of said first member defining a receptacle for receiving at least a portion of the teeth of one of the user's upper or lower jaws, said second side of said first member having a first plurality of fasteners projecting outwardly therefrom, said first plurality of fasteners being formed by a plurality of elongate, parallel extending first projections defining elongate, parallel extending voids between adjacent ones of said first projections, each of said first projections extending in a direction parallel with said second side of said first member, each of said first projections having a neck portion and a retaining head wherein said retaining head is disposed distal of said neck portion and has a width greater than said neck portion;

a second arcuate member having a first side and an opposite second side, said first side of said second member defining a receptacle for receiving at least a portion of the teeth of the other of the user's upper or lower jaws, said second side of said second member having a second plurality of fasteners projecting outwardly therefrom, said second plurality of fasteners being formed by a plurality of elongate, parallel extending second projections defining elongate, parallel extending voids between adjacent ones of said second projections, each of said second projections extending in a direction parallel with said second side of said second member, each of said second projections having a neck portion and a retaining head wherein said retaining head is disposed distal of said neck portion and has a width greater than said neck portion; and said first and second plurality of fasteners being selectively mutually engageable by disposing at least one of said first projections in a void defined between said second projections and disposing at least one of said second projections in a void defined between said first projections wherein mutual engagement of said first and second plurality of fasteners secures said first arcuate member relative to said second arcuate member, said first and second members being selectively securable together in a plurality of configurations defining a plurality of relative positions between the user's upper and lower jaws when said first and second members are mounted thereon.

2. The device of claim 1 wherein each of said first and second arcuate members has a substantially common design.

3. The device of claim 2 wherein each of said first and second plurality of fasteners define at least one substantially unobstructed passageway between said first and second members extending from a central interior position relative to said first and second members to an exterior position relative to said first and second members wherein said unobstructed passageways defined by said first and second plurality of fasteners are in communication and together define a common passageway whereby, during usage of said device, said common passageway provides a breathing airway for the user and wherein each of said unobstructed passageways has a width of at least about 1 millimeter and side edges which are bounded by a respective one of said first and second plurality of fasteners.

4. The device of claim 3 wherein each of said first and second plurality of fasteners defines two unobstructed passageways defining a substantially V-shaped orientation.

5. The device of claim 4 wherein each of said first and second members defines an interior arcuate perimeter and an exterior arcuate perimeter and said two unobstructed passageways defined on each of said first and second members extends from said interior arcuate perimeter to said exterior arcuate perimeter and form openings along each of said respective interior arcuate perimeters that extend for substantially the entire length of said respective interior arcuate perimeter.

6. The device of claim 5 wherein each of said retaining heads of said first and second plurality of fasteners defines a passage extending therethrough for the full length of each respective retaining head.

7. The device of claim 2 further comprising a moldable material disposed within said receptacles of each of said first and second members whereby said receptacles are moldably conformable to the user's teeth.

8. An anti-snoring device for mounting on the teeth of a user's upper and lower jaws, said device defining a centerline and comprising:
   a first arcuate member having a first side and an opposite second side, said first side of said first member defining a receptacle for receiving at least a portion of the teeth of one of the user's upper or lower jaws, said second side of said first member having a first plurality of fasteners projecting outwardly therefrom, said first plurality of fasteners being formed by a plurality of elongate, parallel extending first projections defining elongate, parallel extending voids between adjacent ones of said first projections, said elongate first projections extending in a direction substantially transverse to the centerline and parallel with said second side of said first member;
   a second arcuate member having a first side and an opposite second side, said first side of said second member defining a receptacle for receiving at least a portion of the teeth of the other of the user's upper or lower jaws, said second side of said second member having a second plurality of fasteners projecting outwardly therefrom, said second plurality of fasteners being formed by a plurality of elongate, parallel extending second projections defining elongate, parallel extending voids between adjacent ones of said second projections, said elongate second projections extending in a direction substantially transverse to the centerline and parallel with said second side of said second member; and
   said first and second plurality of fasteners being selectively mutually engageable by disposing at least one of said first projections in a void defined between said second projections and disposing at least one of said second projections in a void defined between said first projections whereby said first and second members can be secured together in a plurality of configurations defining a plurality of relative positions between the user's upper and lower jaws when said first and second members are mounted thereon.

9. The device of claim 8 wherein each of said first and second arcuate members has a substantially common design.

10. The device of claim 9 wherein each of said first and second projections defines a neck portion and a retaining head, said retaining head being disposed distal of said neck portion and having a width greater than said neck portion.

11. The device of claim 10 wherein each of said retaining heads of said first and second plurality of fasteners defines a passage extending therethrough for the full length of each respective retaining head.

12. The device of claim 9 further comprising a moldable material disposed within said receptacles of each of said first and second members whereby said receptacles are moldably conformable to the user's teeth.

13. The device of claim 8 wherein each of said first and second plurality of fasteners define at least one substantially unobstructed passageway between said first and second members extending from a central interior position relative to said first and second members to an exterior position relative to said first and second members and wherein said unobstructed passageways defined by said first and second plurality of fasteners are in communication and together define a common passageway whereby, during usage of said device, said common passageway provides a breathing airway for the user.

14. The device of claim 13 wherein each of said first and second plurality of fasteners defines two unobstructed passageways defining a substantially V-shaped orientation.

15. The device of claim 14 wherein each of said first and second members defines an interior arcuate perimeter and an exterior arcuate perimeter and said two unobstructed passageways defined on each of said first and second members extends from said interior arcuate perimeter to said exterior arcuate perimeter and form openings along each of said respective interior arcuate perimeters that extend for a majority of said respective interior arcuate perimeter.

16. An anti-snoring device for mounting on the teeth of a user's upper and lower jaws, said device defining a centerline and comprising:
   a first arcuate member having a substantially C-shaped cross section defining a receptacle for receiving at least a portion of the teeth of one of the user's upper or lower jaws, said first member having a first plurality of fasteners disposed on said C-shaped cross section opposite an opening of said receptacle and projecting outwardly from said first member, said first plurality of fasteners being formed by a plurality of elongate, parallel extending first projections defining elongate, parallel extending voids between adjacent ones of said first projections, said elongate first projections extending in a direction substantially transverse to the centerline and parallel with a side of said first member from which said first projections project outwardly, each of said first projections having a neck portion and a retaining head wherein said retaining head is disposed distal of said neck portion and has a width greater than said neck portion;
   a second arcuate member having a substantially C-shaped cross section defining a receptacle for receiving at least a portion of the teeth of the other of the user's upper or lower jaws, said second member having a second plurality of fasteners disposed on said C-shaped cross section opposite an opening of said receptacle and projecting outwardly from said second member, said second plurality of fasteners being formed by a plurality of elongate, parallel extending second projections defining elongate, parallel extending voids between adjacent ones of said second projections, said elongate second projections extending in a direction substantially transverse to the centerline and parallel with a side of said second member from which said second projections project outwardly, each of said second projections having a neck portion and a retaining head wherein said retaining head is disposed distal of said neck portion and has a width greater than said neck portion;
   said first and second plurality of fasteners being selectively mutually engageable by disposing at least one of said first projections in a void defined between said second projections and disposing at least one of said second projections in a void defined between said first projections thereby placing at least a portion of said retaining heads of said first and second plurality of fasteners into mutual engagement and securing said first arcuate member relative to said second arcuate member, said first and second members being selectively securable together in a plurality of configurations defining a plurality of relative positions between the user's upper and lower jaws when said first and second members are mounted thereon; and
   wherein each of said first and second arcuate members has a substantially common design.

17. The device of claim 16 wherein each of said first and second plurality of fasteners define at least one substantially unobstructed passageway between said first and second members extending from a central interior position relative to said first and second members to an exterior position relative to said first and second members wherein said unobstructed passageways defined by said first and second plurality of fasteners are in communication and together define a common passageway whereby, during usage of said device, said common passageway provides a breathing airway for the user and wherein each of said unobstructed passageways has a width of at least about 1 millimeter and side edges which are bounded by a respective one of said first and second plurality of fasteners.

18. The device of claim 17 wherein each of said first and second plurality of fasteners defines two unobstructed passageways defining a substantially V-shaped orientation.

19. The device of claim 18 wherein each of said first and second members defines an interior arcuate perimeter and an exterior arcuate perimeter and said two unobstructed passageways defined on each of said first and second members extends from said interior arcuate perimeter to said exterior arcuate perimeter and form openings along each of said respective interior arcuate perimeters that extend for substantially the entire length of said respective interior arcuate perimeter.

20. The device of claim 19 wherein each of said retaining heads of said first and second plurality of fasteners defines a passage extending therethrough for the full length of each respective retaining head.

21. The device of claim 16 further comprising a moldable material disposed within said receptacles of each of said first and second members whereby said receptacles are moldably conformable to the user's teeth.

* * * * *